United States Patent [19]
Frazier et al.

[11] Patent Number: 4,713,458
[45] Date of Patent: Dec. 15, 1987

[54] PREPARATION OF ETHENYLIDENES

[75] Inventors: Kevin A. Frazier, Midland, Mich.; James M. Renga, Walnut Creek, Calif.

[73] Assignee: The Dow Chemical Company, Midland, Mich.

[21] Appl. No.: 642,859

[22] Filed: Aug. 21, 1984

Related U.S. Application Data

[63] Continuation-in-part of Ser. No. 487,537, Apr. 23, 1983, abandoned.

[51] Int. Cl.$^4$ .............. C07D 491/044; C07D 319/08; C07D 213/14
[52] U.S. Cl. .................................. 546/115; 546/270; 546/350; 549/434; 568/630; 568/648; 570/189; 585/603; 585/605; 585/606; 585/607; 585/435; 585/638

[58] Field of Search ............... 546/115, 350, 270; 549/434; 568/630, 648; 570/189; 585/435, 638, 603, 605, 606, 607

[56] References Cited

PUBLICATIONS

Fieser and Fieser, Advanced Organic Chemistry, pp. 482–485, Reinhold Pub. Corp., QD 251 F5a C.4, (1961).
Roberts et al., Basic Principles of Organic Chemistry, pp. 1214–1215, Benjamin Pub. QD 251 R58 C.6.
Buehler et al., Survey of Organic Synthesis, pp. 141–143, Wiley–Interscience Pub. QD 262 B7 C.5, (1970), (I).
Buehler et al., Survey of Organic Synthesis, pp. 156–157, Wiley–Interscience Pub. QD 262 B.7 C.3, (1977), (II).

Primary Examiner—Alan L. Rotman

[57] ABSTRACT

Ketones and aldehydes are converted to ethenylidene-containing compounds by reaction thereof with dimethyl carbonate and a phosphine compound.

17 Claims, No Drawings

PREPARATION OF ETHENYLIDENES

CROSS-REFERENCE TO RELATED APPLICATION

This application is a continuation-in-part application of application Ser. No. 487,537, filed Apr. 23, 1983, abandoned.

BACKGROUND OF THE INVENTION

The present invention relates to the preparation of organic compounds containing olefinic unsaturation. More particularly, the present process is concerned with a method of converting carbonyl functionality in an aldehyde or ketone to ethenylidene functionality under mild conditions without the formation of substantial amounts of undesired by-products.

It is previously known to convert ketones and aldehydes to ethylene-containing compounds (hereinafter referred to as methylenation process) by the use of a Grignard reagent. According to the two-step process, the aldehyde or ketone is reacted with methyl Grignard to prepare an intermediate alcohol which upon dehydration with acid gives an isomeric mixture of olefins. Additional rearrangement of acid labile compounds can occur during the dehydration step.

The Wittig reaction and modifications thereof avoid the formation of isomeric olefins as in the Grignard reaction, but disadvantageously employs multiple steps, the preparation of a phosphonium salt, deprotonation thereof and subsequent reaction with a carbonyl compound. Aldehydes and enolizable ketones are employed only with great difficulty or may not be employed at all.

It is also known to generate the Wittig reagent in situ. Shen et al., U.S. Pat. No. 4,061,759. Buehler et al., *Survery of Organic Synthesis*, Vol. 2, 157 (1977).

It is further known to treat carbonyl-containing compounds with a mixture of carbon tetrachloride or carbon tetrabromide and triphenyl phosphine to prepare a $\beta,\beta$-dihaloolefin, R. Rabinowitz et al., *J.A.C.S.*, 84, 1312 (1962).

Recently various organometallic methylenation reagents have also been disclosed. Included are methylene-bridged complexes of titanium and aluminum disclosed by F. N. Tebbe et al., *J.A.C.S.*, 100, 3611 (1978) and titanium metallocycles disclosed by R. H. Grubbs et al., *J.A.C.S.*, 102, 3270 (1980).

SUMMARY OF THE INVENTION

The present invention provides a process preparing ethenylidene-containing compounds corresponding to the formula:

wherein R and R' are individually the same or different monovalent suitably inert organic radicals or R and R' are collectively a suitably inert divalent organic radical capable of forming a ring having the

moiety as a member of said ring. The process comprises contacting a carbonyl-containing compound corresponding to the formula:

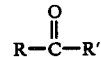

where R and R' are as previously defined with dimethyl carbonate in the presence of a phosphine compound under conditions sufficient to form the desired ethenylidene compound.

For purposes of this invention, an organic radical is suitably inert if it does not interfere with the methylenation of the carbonyl compound.

The products formed by the process include carbon dioxide, methanol, a phosphine oxide and the desired ethenylidene-containing compound. The process proceeds rapidly in a single reaction vessel to produce high yields of the Wittig olefination product with no salt by-products. The olefin products are extremely valuable because of their ability to polymerize by means of the ethylenic unsaturation. They are useful as monomers, cross-linking agents and polymerization initiators.

DETAILED DESCRIPTION OF THE INVENTION

The ketone or aldehyde reactant (carbonyl compound) employed in the present invention is well-known or may be prepared by well-known processes. Most suitable are those carbonyl compounds suitably employed in known Wittig reactions. Examples include compounds of the previously defined formula R—C(O)—R' wherein R is alkyl, cycloalkyl, cycloalkenyl, aryl, alkaryl or aralkyl, or such groups further containing nitrogen, sulfur, halogen or oxygen atoms; R' is alkylene or arylene or hydrogen. Preferably, R is phenyl, alkyl, alkylphenyl, or an alkoxy- or hydroxy-substituted derivative thereof, R' is phenylene or hydrogen. Most preferably, R is phenyl or $C_{1-20}$ alkyl and R' is hydrogen.

Suitable phosphine reactants are triorgano phosphines. Preferred are triaryl phosphines optionally ring-substituted with halo or alkoxy groups. While trialkyl phosphines are suitably employed, some by-products may result if abstractable protons are present. For example, butylidene products result from the use of tri(n-butyl)phosphine. Additional suitable organo phosphines include polymeric compounds, such as polymer-bound phosphines, e.g., a phosphine functionalized styrene-divinylbenzene copolymer. A preferred catalyst is triphenyl phosphine.

According to the process the ketone or aldehyde reactant, dimethyl carbonate and phosphine reactant are combined in any convenient order in a suitable reaction vessel such as metal, glass or glass-lined reactors and reacted at the desired temperature. Any operational temperature may be used. Elevated temperatures from about 120° C. to about 220° C., preferably from about 130° C. to about 200° C., and most preferably from about 150° C. to about 175° C. are generally employed. Because the reaction produces carbon dioxide, it is advantageous to either employ pressure-containing means or suitably vent the volatile reaction products.

The reactants may be combined in any amount, however, preferably a slight excess of dimethyl carbonate and phosphine are employed. Suitably the ratio of ketone or aldehyde reactant, dimethyl carbonate and phosphine reactant in equivalents is from about 1.0:1.0:1.0 to about 1.0:2.0:2.0. Preferably an excess of dimethyl carbonate and phosphine reactants are employed, e.g., a ratio based on equivalents of from about 1.0:1.1:1.1 to about 1.0:1.5:1.5.

It has been found that a catalytic amount of a soluble source of halide ions, e.g., a halide compound, may be employed as an initiator to increase the rate of reaction, if desired. The halide ion may be introduced in any suitable method. Suitable methods include the use of $C_{1-4}$ alkyl halide, expecially methyl halides such as methyl iodide or methyl chloride. The latter, however, is slightly more difficult to handle due to the inconvenience of employing gaseous reactants. Alternatively, halide may be introduced by use of a phosphonium or ammonium halide salt. Suitable amounts of halide are from about 0.01 equivalents to about 0.1 equivalents of halide compound per equivalent of dimethyl carbonate.

In one embodiment of the present invention, a suitable inert liquid such as toluene or chlorinated aromatics may be employed as a solvent. However, preferably no solvent is employed to simplify separation of the desired reaction products.

It is possible according to the invention to add a small amount of a free radical inhibitor to the reaction mixture in order to prevent premature polymerization of the ethenylidene product without departing from the scope of the present invention. Suitable inhibitors include the quinone compounds such as methyl hydroquinone.

It is believed without wishing to be bound by such belief that the present invented process operates by the generation in situ of a phosphorus ylid that is subsequently trapped by reaction with the carbonyl-containing compound thereby resulting in the methylenation reaction. Accordingly, the skilled artisan will be readily apprised that certain carbonyl compounds, such as those containing $\alpha,\beta$-unsaturation, halogenated aliphatic compounds and exceptionally hindered substances are normally not employed in the Wittig process due to generation of large amounts of by-products in addition to the desired methylenated product. Suitable ketone or aldehyde reactants are easily verified by noting the formation of unacceptable amounts of by-products from the reaction.

A preferred embodiment of the process produces compounds corresponding to the formula:

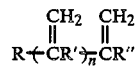

wherein R is a monovalent $C_{1-20}$ organic radical; R' is a divalent $C_{1-20}$ organic radical; R'' is hydrogen or a monovalent $C_{1-20}$ organic radical; and n is an integer from zero to about 10, comprising contacting a carbonyl-containing compound corresponding to the formula,

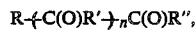

wherein R, R', R'' and n are as previously defined with dimethyl carbonate in the presence of a phosphine compound at an elevated temperature.

SPECIFIC EMBODIMENTS

Having described the invention, the following examples are provided as further illustration and not limitation of this invention as many variations and modifications of the examples may be readily apparent to the skilled artisan not departing from the scope of the present invention.

Example 1

In a 300-ml Parr pressure reactor equipped with a mechanical stirrer, acetophenone (12 g, 100 mmoles), dimethyl carbonate (13.5 g, 150 mmoles), triphenyl phosphine (23.1 g, 150 mmoles), ethyltriphenyl phosphonium iodide (0.83 g) are combined. The reactor is sealed and heating and stirring commenced. After heating at 175° C. for two hours, the reaction mixture is cooled and the reactor vented. The reactor contents are transferred to a distillation flask. The reactor is rinsed with methylene chloride and the two liquid mixtures combined for distillation. The product α-methylstyrene is recovered by distillation. Isolated yield, 91 percent, based on acetophenone.

Examples 2–14

The procedure of Example 1 is substantially repeated employing the carbonyl-containing reactants further identified in Table I. Most compounds prepared are identified by coinjection of authentic samples on a capillary column gas chromatograph. Further identification is made by comparison with published boiling points. The starting aldehyde for Example 14, the 3,4-α-di-O-isopropylidene derivative of 2-methyl-3-hydroxy-4-hydroxymethyl-5-formylpyridine, is a known compound having been previously described in U.S. Pat. No. 4,061,759, column 13, line 63.

TABLE I

| Example | Carbonyl Reactant | Product | % Isolated Yield |
| --- | --- | --- | --- |
| 2 | benzaldehyde | styrene | — |
| 3 | p-methoxybenzaldehyde | p-methoxystyrene | 83 |
| 4 | p-hydroxybenzaldehyde | p-methoxystyrene | — |
| 5 | 1,3-dibenzoylbenzene | 1,3-bis(1-phenylethenyl)benzene | 98 |
| 6 | 1-methylcyclohexanone | 1-methyl-2-methenylcyclohexane | 83 |
| 7 | cyclohexene-4-carboxaldehyde | vinylcyclohexene | 69 |
| 8 | vinylcyclohexanal[1] | divinylcyclohexane[1] | — |
| 9 | 1-decanal | 1-decene | 64 |
| 10 | p-chlorobenzaldehyde | p-chlorostyrene | 62[2] |
| 11 | 1,3-benzodeoxole-5-carboxaldehyde | 5-ethenyl-1,3-benzodioxole | 84 |
| 12 | 3-pyridine carboxaldehyde | 3-vinyl pyridine | 22 |
| 13 | m-(methoxy)methoxybenzaldehyde | m-(methoxy)methoxystyrene | 81 |

TABLE I-continued

| Example | Carbonyl Reactant | Product | % Isolated Yield |
|---|---|---|---|
| 14 | pyridine aldehyde compound[3] | vinylpyridine derivative[4] | 60 |

[1]Mixture of isomers
[2]Yield determined by gas-liquid chromatogram

[3] 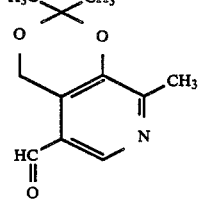

[4] 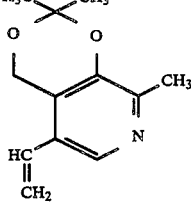

What is claimed is:

1. A process for the preparation of ethenylidene-containing compounds corresponding to the formula:

wherein R and R' are individually the same or different monovalent suitably inert $C_{1-20}$ organic radicals, or R and R' are collectively a suitably inert divalent organic radical capable of forming a ring having the

moiety as a member of said ring comprising contacting a carbonyl-containing compound corresponding to the formula:

where R and R' are as previously defined with dimethyl carbonate in the presence of a triorgano phosphine compound under conditions sufficient to form the desired ethenylidene compound.

2. A process for the preparation of ethenylidene-containing compounds corresponding to the formula:

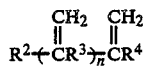

wherein $R^2$ is a monovalent $C_{1-20}$ organic radical; $R^3$ is a divalent $C_{1-20}$ organic radical; $R^4$ is hydrogen or a monovalent $C_{1-20}$ organic radical; and n is an integer from zero to about 10, comprising contacting a carbonyl-containing compound corresponding to the formula,

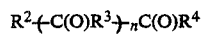

wherein $R^2$, $R^3$, $R^4$ and n are as previously defined with dimethyl carbonate in the presence of a triorgano phosphine compound at an elevated temperature.

3. A process according to claim 2 wherein R is alkyl, cycloalkyl, cycloalkenyl, aryl, alkaryl or aralkyl, or such group further containing nitrogen, sulfur, halogen or oxygen atoms; $R^3$ is alkylene or arylene; and $R^4$ is $R^2$ or hydrogen.

4. A process according to claim 2 wherein $R^2$ is alkyl, cycloalkyl, cycloalkenyl, aryl, alkaryl or aralkyl, or such group further containing nitrogen, sulfur, halogen or oxygen atoms; $R^3$ is alkylene or arylene; and $R^4$ is $R^2$ or hydrogen.

5. A process according to claim 3 wherein R is phenyl, alkyl, alkylphenyl or an alkoxy- or hydroxy-substituted derivative thereof; $R^3$ is phenylene; n is zero or one; and $R^4$ is hydrogen or $R^2$.

6. A process according to claim 4 wherein R is phenyl or $C_{1-20}$ alkyl, n is zero and $R^4$ is hydrogen.

7. A process according to claim 6 wherein the phosphine compound is a triaryl phosphine optionally ring-substituted with halo or alkoxy groups.

8. A process according to claim 1 or 2 wherein the triorgano phosphine compound is triphenyl phosphine.

9. A process according to claim 1 or 2 wherein the temperature is from about 120° C. to about 220° C.

10. A process according to claim 8 wherein the temperature is from about 130° C. to about 200° C.

11. A process according to claim 9 wherein the temperature is from about 150° C. to about 175° C.

12. A process according to claim 1 or 2 wherein the carbonyl-containing compound, dimethyl carbonate and phosphine compound are combined in an equivalent ratio of from about 1.0:1.0:1.0 to about 1.0:2.0:2.0.

13. A process according to claim 11 wherein the carbonyl-containing compound, dimethyl carbonate and phosphine compound are combined in an equivalent ratio of from about 1.0:1.1:1.1 to about 1.0:1.5:1.5.

14. A process according to claim 1 or 2 wherein in addition, a catalytically effective amount of a halide source is additionally present.

15. A process according to claim 14 wherein the halide source is a halide compound, selected from the group consisting of a $C_{1-4}$ alkyl halide, a phosphonium halide and an ammonium halide.

16. A process according to claim 14 wherein the $C_{1-4}$ alkyl halide is a methyl halide.

17. A process according to claim 14 wherein from about 0.01 to about 0.1 equivalent of halide compound per equivalent of dimethyl carbonate is employed.

* * * * *

UNITED STATES PATENT AND TRADEMARK OFFICE
CERTIFICATE OF CORRECTION

PATENT NO. : 4,713,458

DATED : December 15, 1987

INVENTOR(S) : Kevin A. Frazier; James M. Renga

It is certified that error appears in the above-identified patent and that said Letters Patent is hereby corrected as shown below:

Column 3, line 11, "expecially" should read --especially--.

Signed and Sealed this

Twenty-first Day of February, 1989

Attest:

DONALD J. QUIGG

*Attesting Officer*     *Commissioner of Patents and Trademarks*